United States Patent [19]

Friedman et al.

[11] Patent Number: 5,480,895
[45] Date of Patent: Jan. 2, 1996

[54] METHOD OF PRODUCING ANTIBODIES TO A RESTRICTED POPULATION OF T LYMPHOCYTES, ANTIBODIES PRODUCED THEREFROM AND METHODS OF USE THEREOF

[75] Inventors: Steven M. Friedman, Tenafly, N.J.; Mary K. Crow; David Posnett, both of New York, N.Y.

[73] Assignee: New York Society for the Relief of the Ruptured and Crippled, Maintaining the Hospital for Special Surgery, New York, N.Y.

[21] Appl. No.: 766,751

[22] Filed: Sep. 27, 1991

[51] Int. Cl.⁶ .................................................. G01N 33/577
[52] U.S. Cl. ................. 435/7.24; 435/70.21; 435/172.2; 436/547; 436/548; 530/388.22; 530/388.75
[58] Field of Search .............................. 435/7, 24, 70.21, 435/172.2, 948; 436/547, 548; 530/388.22, 388.75

[56] References Cited

FOREIGN PATENT DOCUMENTS

WO91/06319  5/1991  WIPO.
WO91/12818  9/1991  WIPO.

OTHER PUBLICATIONS

The Journal of Experimental Medicine, vol. 174, No. 4, 1 Oct. 1991, pp. 891–900.

*Primary Examiner*—David Saunders
*Attorney, Agent, or Firm*—Darby & Darby

[57] ABSTRACT

This invention relates to a method of obtaining antibodies specific to a population of T-lymphocytes (T cells) restricted by Vβ gene usage. The invention also relates to the antibodies obtained and to methods of using them. According to the invention, T cells are incubated with an effective amount of a superantigen under conditions and for a time sufficient to allow division and growth of T-cells reactive to the superantigen. The incubated T-cells are injected into a mammal, and thereafter serum containing antibodies specific to the incubated and injected T-cells is removed from the mammal.

14 Claims, 5 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

CTTCTGATGG CTCAAACAC 19

( 2 ) INFORMATION FOR SEQ ID NO:2:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GAACCCTGAC CCTGCCGT 18

( 2 ) INFORMATION FOR SEQ ID NO:3:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:3:

TCATAAATTC GGGTAGGATC 20

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

GTTTCTCATC AACCATGCAA 20

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TCAGGTGTGA TCCAATTTC 19

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GTCAGGGGCC CCAGTTTAT 19

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

ACAGCGTCTC TCGGGAGA 18

METHOD OF PRODUCING ANTIBODIES TO A RESTRICTED POPULATION OF T LYMPHOCYTES, ANTIBODIES PRODUCED THEREFROM AND METHODS OF USE THEREOF

This invention was made in part with support under grants CA-49283, AI-28367, AI-31140, CA-42046, AR-02255, AI-12103 and P60-AR-38520 awarded by the National Institutes of Health. The Government has certain rights in the invention.

BACKGROUND OF THE INVENTION

This invention relates to a method of obtaining antibodies specific to a population of T lymphocytes (T cells, TCL) restricted by Vβ gene usage, antibodies thus obtained and methods of use thereof.

More than 95% of all T cells have a cell surface receptor designated the "T-cell receptor" (hereinafter, "TCR"). For a review of T cell ontogeny, see Moyer and Reinherz, "T Lymphocytes: Ontogeny, Function, and Relevance to Clinical Disorders", N. Engl. J. Med., 317:1136–1142 (1987). TCR consists of a clonotypic Ti α-β heterodimer with an apparent molecular weight (Mw) of 90 kD and a monomorphic T3 molecule containing five subunits ($\gamma, \delta, \zeta, \epsilon$, and $\eta$). The γ subunit has an apparent Mw of 25 kD, the δ and ε subunits each have an apparent Mw of 20 kD, the ζ subunit has an apparent Mw of 16 kD, and the η subunit an apparent Mw of 22 kD. All five receptor subunits are transmembrane proteins. As is the case with antigen-binding heavy and light chains of immunoglobulin proteins, TCR α and β proteins contain both variable (hereinafter "V") and constant (hereinafter "C") regions. For a review of immunoglobulin proteins and gene usage, see Lewin, *Genes III*, John Wiley & Sons, Inc. pp. 642–653 (1987), which is incorporated herein by reference.

It appears that the Ti subunits form a binding site for antigen and the major histocompatibility complex (hereinafter "MHC") through interaction of their V domains. Antigen recognition is important for activation of both cytotoxic effector T cells and immunoregulatory T cells. Cytotoxic T cells lyse specific target cells, including tumor cells and virus-infected cells, whereas immunoregulatory T cells induce or suppress the cells of the immune system either directly or indirectly through lymphokines.

Analyses of many of the cDNA nucleotide sequences encoding a variety of β chains have led to the recognition of structural similarity between genes encoding β chains and genes encoding immunoglobulins. Thus, genes encoding β chains contain V, constant (C), joining (J) and diversity (D)-like elements The present invention is concerned with the V region of the chain, hereinafter termed Vβ. In humans, approximately 57 Vβ genes are known to exist in the Ti β locus on chromosome 7 at 7q35 Robinson, "The Human T Cell Receptor β-chain Gene Complex Contains at Least 57 Variable Gene Segments", J Immunol , 146:4392–4397 (1991)

T cell proliferation requires the interaction of the Ti complex with antigen and interleukin-2 (hereinafter "IL-2"). Although resting T cells express no receptors for IL-2; after the T cell receptors are activated by antigen and MHC, induction of IL-2 receptors occurs within hours The activation also leads to endogenous induction and secretion of IL-2, DNA synthesis and cell mitosis.

Various disease states and physiological disorders are associated with T cell dysfunctions. These disorders, are characterized by a particular subset, or restricted population, of T cells which are thought to be responsible for the dysfunction The restricted population is recognized by its expression of only one or a few related types of TCR and can be monitored by the type of Vα and/or Vβ gene expressed. A restricted set of T cells is one in which the T cells express one or a few common V genes but are otherwise dissimilar By comparison, a clonal population of T cells, such as may be derived from a tumor, is a population of T cells that are the progeny of a single cell and are hence virtually identical.

Disorders thought to be caused by T cell dysfunctions include but are not limited to various autoimmune diseases such as systemic lupus erythematosus multiple sclerosis, myasthenia gravis, diabetes mellitus, and various forms of arthritis such as rheumatoid arthritis. These dysfunctions are characterized by the expansion of a restricted T cell population that expresses one or a few Vβ genes from a Vβ family. Different patients express a single Vβ but not necessarily the same Vβ gene as another patient. For instance, expanded T cell populations from MS patients express one of the V genes from the related group of Vβ12, Vβ13, Vβ14, Vβ15 and Vβ17. Several methods of therapy have been proposed based on eliminating or blocking the T cell population responsible for a dysfunction. For review see Janeway, "Immunotherapy by Peptides" Nature 341:482–483 (1989); and Hashim et al., "Antibodies for Vβ8 Receptor Peptide Suppress Experimental Autoimmune Encephalomyelitis", J. Immunol., 144:4621–4627 (1990), which are incorporated herein by reference.

There is considerable evidence of selective TCR Vβ gene usage among rodent T cells which mediate a number of experimental autoimmune diseases. For example, in experimental allergic encephalomyelitis (EAE), Vβ8.2$^+$ T cells play a central role. In five different strains of rats, encephalitogenic T cell clones and hybridomas, reactive against myelin basic protein (MBP) peptide fragments, were found to be uniformly Vβ8.2$^+$. Burns et al., "Both Rat and Mouse TcRs Specific for the Encephalitogenic Determinant of MBP use Similar Vα and Vβ Chain Genes Even Though the MHC and Encephalitogenic Determinants Being Recognized are Different", J. Exp. Med., 169:27 (1989). Similarly, Vβ8.2 is expressed on over 85% of T cells reacting to the encephalitogenic MBP peptide in strains of mice susceptible to EAE. Acha-Orbea et al., "Limited Heterogeneity of T Cell Receptors From Lymphocytes Mediating Autoimmune Encephalomyelitis Allows Specific Immune Intervention" Cell 54:563 (1988); and Urban et al , "Restricted Use of T Cell Receptor Genes in Murine Autoimmune Encephalomyelitis Raises Possibilities for Antibody Therapy", Cell, 54:577 (1988). The mouse Vβ8 gene family products are homologous to the human Vβ12, Vβ13, Vβ14, Vβ15 and Vβ17 gene products.

The in vivo administration of mAb specific for Vβ8.2 has been shown to both protect mice from the development of EAE induced by a subsequent challenge with MBP, and to ameliorate the clinical course of EAE in mice already affected. Acha-Orbea et al. (1988). It has also been found that EAE can be vaccinated against. In this case, the anti-T cell response is mediated by another set of T cells Lohse et al,. "Control of Experimental Autoimmune Encephalomyelitis by T Cells Responding to Activated T Cells", Science, 244:820–824 (1989).

In another animal disease model, collagen-induced arthritis, T cells reactive against type II collagen which are capable of transferring arthritis to naive syngeneic mice are virtually all Vβ8.2+ Banerjee et al., "Possible Role of Vβ T Cell Receptor Genes in Susceptibility to Collagen-Induced Arthritis in Mice", J Exp Med, 167:832 (1988). These observations suggest that expression of the Vβ8.2 gene product may be associated with an autoimmune T cell pool in rodents, for instance, T cells derived from the CD4−CD8− Vβ8.2 expressing thymocyte subpopulations. Fowlkes et al., "A Novel Population of T Cell Receptor αβ Bearing Thymocytes Which Predominantly Express a Single Vβ Gene Family", Nature, 329:251 (1987); Shortman et al., "Mouse Strain Differences in Subset Distribution and T Cell Antigen Receptor Expression Among CD4−CD8− Thymocytes", Immunol. Cell Biol., 66:423 (1988); and Takahama et al., "Phenotype, Ontogeny, and Repertoire of CD4−CD8− T Cell Receptor αβ+ Thymocytes: Variable Influence of Self-Antigens on T Cell Receptor Vβ Usage", J. Immunol., 146:1134 (1991).

Recently, it has been possible to determine the TCR gene usage of a population of T cells. Bertness et al., "T cell Receptor Gene Rearrangements as Clinical Markers of Human T cell Lymphomas", N. Engl. J. Med., 313:534–538 (1985). Such determinations have relied on anticlonotypic antibodies directed at epitopes found on V domains of TCR and cDNA probes that detect clone-specific DNA rearrangements. However, the availability of anticlonotypic antibodies and cDNA probes has been limited to the availability of naturally occurring clonal populations of T cells such as from tumors. This drawback renders these methods less clinically applicable than would be the case if a wide variety of antibodies were available to the full range of TCR V gene products associated with T cell dysfunctions. This is particularly important in T cell dysfunctions which are characterized by restricted rather than clonal populations of T cells. It would be useful to have a method of obtaining antibodies specific for the protein products of the TCR V gene families for the purposes of diagnoses and therapeutics of various disorders related to T cell dysfunctions.

SUMMARY OF THE INVENTION

It has now been found that antibodies specific for a restricted set of T cells having common TCR Vβ gene usage can be obtained by incubating T cells with an effective amount of a superantigen (SA) under conditions and for a time sufficient to allow division and growth of T cells reactive to the SA, injecting the incubated T cells into a mammal and obtaining the anti-Vβ antibodies from the mammal.

Additional antibodies can be made to T cells expressing other TCR Vβ genes in the restricted set, by selectively removing, or depleting, T cells recognized by an antibody produced by the method of the present invention. The remaining T cells are injected into a mammal to produce antibodies. The depletion step may be followed by another cycle of SA expansion. Depletion, expansion and injection can be repeated a number of times with a single sample of T cells to provide a panel of antibodies specific for a variety of Vβ gene products each of which recognizes a single restricted set of T cells. Such antibodies and methods for their use are provided.

DETAILED DESCRIPTION OF THE INVENTION

Figure 1:
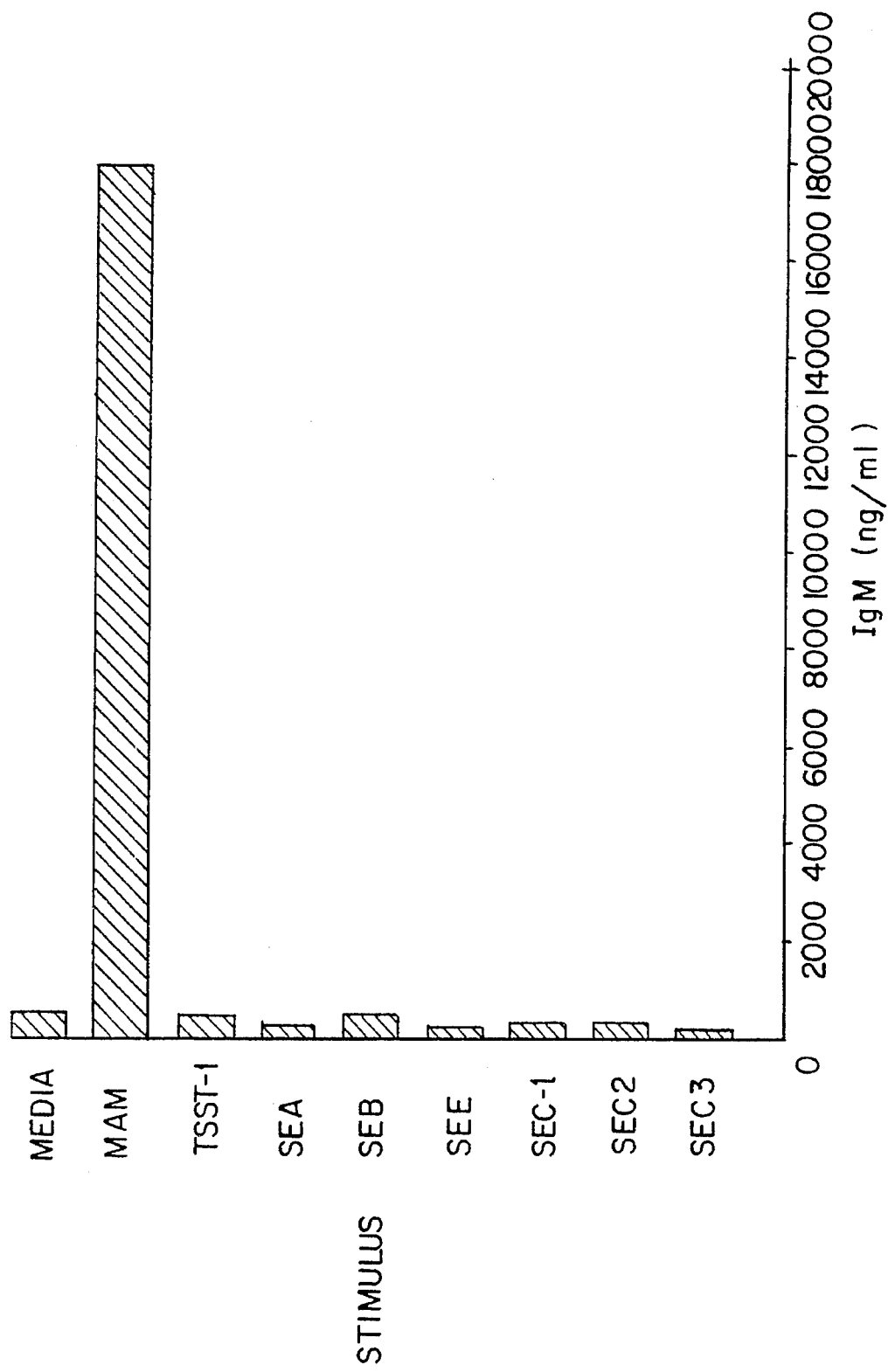
FIG. 1 is a bar graph depicting B cell differentiation in response to T cells exposed to various SA, or media alone. Differentiation is determined by IgM production.

SAs are a group of proteins that activate a large proportion of the T cell repertoire based on dual avidity for MHC class II antigens and TCR epitopes common to products of one or several TCR β chain V gene families. Several SA induce massive T cell proliferation and cytokine secretion and have been implicated in clinical syndromes, frequently those characterized by shock and generalized immunosuppression. SA activation of a more restricted T cell response may also have an effect on the immune system related to autoimmune disorders. Friedman et al., "A Potential Role for Microbial Superantigens in the Pathogenesis of Systemic Autoimmune Disease", Arth & Rheum, 34:468–480 (1991).

SA identified to date include microbial and viral proteins. The microbial SA include several staphyloccal enterotoxins, a fragment of the group a streptococcus M protein, and MAM, a soluble mitogen produced by *Mycoplasma arthritidis*. Unite et al., "The V specific Superantigen Staphylococcal Enterotoxin B: Stimulation of Mature T cells and Clonal Deletion in Neonatal Mice", Cell 56:27–35 (1989); Tomai et al., "Superantigenicity of Streptococcal M Protein", J. Exp. Med., 172:359–362 (1990); and Atkin et al., "Stimulation of Mouse Lymphocytes by a Mitogen Derived from *Mycoplasma arthritidis*V. A Small Basic Protein from Culture Supernatants is a Potent T cell Mitogen", J. Immunol., 137:1581–1589 (1986) which are incorporated herein by reference. Note that *M. arthritidis* is a causative agent of inflammatory arthritis in rodents. Cole and Ward, "Mycoplasma as Arthritogenic Agents", *The Mycoplasmas*, Vol. IV, New York, Academic Press (1979). The microbial toxins that function as SA are among the most potent mitogens known.

MAM, for example, induces half-maximal T cell proliferation at concentrations of less than $1 \times 10^{-11}$M. Atkin et al. (1986). Virally encoded SA are typified by those encoded by the mouse mammary tumor virus. Choi et al., "A Superantigen Encoding in the Open Reading frame of the 3' Long Terminal Repeat of Mouse Mammary Tumour Virus", Nature, 350:203–207 (1991).

In the mouse, MAM has been shown to behave as a classic microbial SA, selectively inducing the proliferation of V$\beta 8^+$ and V$\beta 6^+$ murine T Cells. Cole et al., "Stimulation of Mouse Lymphocytes by a Mitogen Derived From *M. arthritides*. VII. Responsiveness is Associated With Expression of a Product(s) of the V$\beta 8$ Gene Family Present on the T cell Receptor $\alpha/\beta$ for Antigen", J. Immunol., 142:4131 (1989). While MAM is mitogenic for human T cells, the level of proliferation induced is quite modest compared to that triggered by the *S. aureus*-derived SA, and no data exist regarding TCR V gene dependence of MAM recognition. It has now been found that MAM-reactive human T cells utilize a restricted group of TCR V$\beta$ gene products. Monoclonal antibody (mAb) C1, the mAb described herein which was generated by the immunization of mice with a nonclonal MAM-reactive human T cell line, recognizes a disulfide linked heterodimer, consistent with the $\alpha/\beta$ TCR, on approximately 3–6% of peripheral T cells, and 40–60% of MAM reactive T cells.

As with other mAb specific for TCR V gene products, C1 reacts with a small fraction of both the CD4$^+$ and CD8$^+$ subsets of all donors tested, including cord blood T cells. With respect to SA recognition, it was determined that MAM-reactive TCL are greatly enriched in C1$^+$ cells, while TCL responsive to SA with which MAM-reactive TCL are less crossreactive, SEE and TSST-1, are depleted of C1$^+$ T cells. Studies employing the polymerase chain reaction to amplify TCR $\beta$ chain cDNA from C1$^+$ TCL cells demonstrate that C1 identifies an epitope expressed on the V$\beta 17$ gene product. Taken together, these results show that MAM recognition by human T cells is restricted by TCR V$\beta$ gene usage and that a major fraction of MAM-reactive human T cells are V$\beta 17^+$.

The present invention thus includes antibodies produced by the methods described herein. In particular, mAb C1 is encompassed by the present invention. mAb C1 has been deposited in the American Type Culture Collection (ATCC) and been given accession HB 10874.

It has now been found that mAb C1 is a unique example of a TCR V gene specific mAb generated by immunizing with a restricted T cell population. As discussed above, MAM is a relatively weak mitogen for human T cells, suggesting a restricted population of MAM-reactive T cells. MAM is thus the preferred SA for use in the present invention, however, any other SA is embodied by the present invention. Staining data demonstrate that the TCR epitope recognized by mAb C1 is expressed not only on >60% of the immunizing TCL, which had been retriggered repetitively with MAM, but is also present on a relatively large fraction of peripheral T cells activated by MAM for only several days in primary short term cultures (Table III). The successful application of this method, utilizing TCL responsive to other microbial SA as immunogens, or MAM reactive T cells depleted of C1$^+$ T cells greatly expands the available panel of mAbs against human TCR V gene products.

Utilizing mAb C1 to determine what percentage of T cells are recognized by C1, it was found that on average, C1$^+$ T cells represent approximately 3–5% of the peripheral T cell pool. The marked enrichment of C1$^+$ T cells in even short-term cultures of MAM activated PBL, provide strong, albeit indirect, evidence that all C1$^+$ T cells are MAM reactive.

Additionally, subsets of MAM-reactive T cells express V$\beta$ genes other than V$\beta 17$, the population recognized by mAb C1. These other subsets were shown to exist by several lines of evidence. First, resting peripheral blood T cells, depleted of C1$^+$ cells, show an undiminished proliferative response to MAM over a wide range of SA concentrations. Second, only 40–60% of T cells which persist in long term cultures maintained by repetitive retriggering with MAM plus autologous APC are C1$^+$. Third, MAM reactive TCL which have been depleted of C1$^+$ T cells exhibit potent, SA specific lysis of MAM bearing target cells. The method described herein can thus be utilized to identify other V$\beta$ genes used by MAM-reactive T cells and to generate mAbs against their products. Such a method is facilitated by depleting the MAM reactive cells of C1$^+$ T cells, re-expanding the remaining T cells with MAM and using the resulting cells to induce antibody production. Subsequently produced antibodies can then be used in repeated rounds of depletion, expansion and antibody production. Depletion of cells recognized by a specific antibody is rapid and efficient. For instance, MAM reactive T cells treated with C1, exposed to goat anti-mouse IgG antibodies linked to iron and exposed to a magnet, are selectively depleted of all C1$^+$ T cells such that they do not reappear even after repeated rounds of expansion with MAM.

The observation that human MAM-reactive T cells identified by mAb C1 are V$\beta 17^+$ is of particular interest in light of the restricted nature of T cells in diseases characterized by T cell dysfunctions. Amino acid sequence analysis has demonstrated considerable homology between the products of murine V$\beta 8$ genes which are expressed by MAM-reactive murine T cells and several human TCR V$\beta$ gene families, including V$\beta 17$, V$\beta 12$, V$\beta 13$, V$\beta 14$ and V$\beta 15$. Cole et al., "Stimulation of Mouse Lymphocytes by a Mitogen Derived from *M. arthritidis*. VIII. Selective Activation of T Cells expressing Distinct V$\beta$ T Cell Receptors From Various Strains of Mice by the 'Superantigen' MAM", J. Immunol., 142:4131 (1989), and Chothia et al., "The Outline Structure of the T Cell $\alpha/\beta$ Receptor", EMBO J., 7:3745 (1988). Moreover, there are reports implicating selective usage of V$\beta 17$ and several other TCR V$\beta$ gene families by autoimmune human T cells. For example, expanded populations of MBP-reactive T cells in the peripheral blood of multiple sclerosis (MS) patients have been reported. In this report each individual MS patient used a particular TCR V$\beta$ gene family for TCR in MBP-reactive T cells. Ben-Nun et al., "Restricted T-cell Receptor V$\beta$ Gene Usage by Myelin Basic Protein-Specific T-cells Clones in Multiple Sclerosis: Predominant Genes Vary in Individuals", Proc. Natl. Acad. Sci. USA, 88:2466–2470 (1991). Preferential usage of V$\beta 17$ as well as V$\beta 12$, V$\beta 14$ and V$\beta 15$ among those T cells reactive against an encephalotogenic MBP peptide presented in association with DR2 and DR3, two MHC class II genes that are over-represented in the MS patient population. Wucherpfennig et al., "Shared Human T Cell Receptor V$\beta$ Usage to Immunodominant Regions of Myelin Basic Protein", Science 248:1016 (1990) In addition, V$\beta 17^+$ T cells have been reported to be enriched among activated T cells isolated from the synovial tissue of patients with rheumatoid arthritis (RA). Howell et al., "Clonal Infiltrates of Activated V$\beta 17^+$ T Cells in Synovial Tissues of Rheumatoid Arthritis Patients", J. Cell Biochem. Suppl., 15A:295 (1991). Another study shows that V$\beta 14^+$ T cells are overrepresented among synovial fluid T cells from patients with rheumatoid arthritis. Pallard and West, Science, 253:325–329 (1991).

According to the method of the present invention, mAb to a non-clonal, but restricted, population of T cells are made as described in detail in the Examples presented below. Briefly, T cells are isolated from whole blood or plasma by any method known in the art. Preferred methods include but are not limited to separation of T cells from non-T cells by the formation of rosettes with SRBC and centrifugation on a Ficoll Hypaque gradient according to standard procedures. The isolated T cells are then incubated with any SA at a concentration of SA sufficient to cause T cell proliferation. Once the SA is added, the cells express the IL-2 receptor such that exogenous IL-2 must be supplied at some point. Generally, IL-2 is not added initially. This is because a small amount of endogenous Il1-2 is produced and is sufficient to stimulate cells that have a strong response to the SA. Exogenous IL-2 is withheld for about one week to prevent proliferation of cells that respond weakly to the SA. After SA treatment, the cells are allowed to grow for a suitable amount of time, usually about two to three weeks under suitable growth conditions.

In order to eliminate T cells expressing TCR Vβ gene products, for which antibodies are already available, the T cells are incubated with an anti-Vβ specific antibody, and subsequently exposed to goat anti-mouse immunoglobulin anti-body. The immune complexes which form between the anti-mouse antibody, the Vβ specific antibody and the T cells recognized by the Vβ specific antibody, are then removed, for instance by magnetic beads and a magnet or fluorescence activated cell sorting (FACS) depending on the selective marker attached to the anti-mouse antibody. After allowing the remaining cells to grow, an optional selection step may be performed utilizing one of the isolation methods described above. The whole cells are then injected into the animal host under conditions suitable to cause antibody formation. The antibodies obtained are screened on the cell line with which the animals were immunized. As a negative control, cells derived from the same donor but treated with a different, non-cross reactive SA can be used.

Immunization with the incubated T cells can be effected by methods including but not limited to subcutaneously, intraperitoneally, intravenously, intramuscularly or directly into lymph nodes.

As with all immunogenic compositions for eliciting antibodies, the immunogenically effective amounts of the T cells must be determined empirically. Factors to be considered are the immunogenicity of the T cells, whether or not the T cells will be complexed with or covalently attached to an adjuvant or carrier protein or other carrier, route of administration, and number of immunizing doses to be administered. Such factors are known in the vaccine art and it is well within the skill of immunologists to make such determinations without undue experimentation.

The number of T cells needed to stimulate antibody production will vary somewhat according to the nature of the T cells (i.e. which Vβ they express) and animal species, in addition to the factors described above. As little as $1\times10^6$ cells may be sufficient to elicit an immune response and up to about $20-100\times10^6$ cells or more could also be used. Preferably, the effective amount to ensure antibody production is about $10\times10^6$ cells for mice. The T cells are not mixed with an adjuvant or adsorbent. Generally, the cells are merely mixed with a physiologically acceptable carrier such as normal saline or a buffering compound suitable for administration to mammals.

The presence of the antibodies of the present invention, either polyclonal or monoclonal, can be determined by various assays. Assay techniques include but are not limited to immunofluorescence (IF) by cytofluorographic analysis or by cell sorting, indirect immunofluoroscence, immunoprecipitation, ELISA, agglutination and Western blot techniques. Analysis of Vβ gene usage can be done by DNA sequencing, preferably a DNA amplification step is added such as polymerase chain reaction (PCR) as described below.

The preferred technique is IF by cytofluorographic analysis rather than by cell sorting. Briefly, about $1\times10^5$ peripheral blood T cells or SA reactive TCL cells are mixed with hybridoma culture supernatants, washed, counterstained with fluorescein labelled goat anti-mouse IgG, washed and examined for immunofluorescence staining on a cytofluorograph, for instance an Ortho IIs. Procedures involving the use of agglutination assays are well known in the art of blood screening. Western blots are performed essentially according to the methods described by Towbin et al., Proc. Natl. Acad. Sci. USA, 76:4350 (1979).

The antibodies obtained by the method of the present invention can be used in methods of detection of the presence of particular populations of T cells bearing the gene products of a TCR Vβ chain family and can be used to quantitate the percentage of these populations of T cells in the total population of T cells. This is useful in diagnosing various diseases related to T cell dysfunctions wherein a particular restricted population of T cell is over-represented within the entire T cell population. Preferably, the methods which use the antibodies to detect the presence of particular types of T cells in a sample involve contacting the sample with at least one of the antibodies under conditions which allow the formation of an immunological complex between the antibody and the specific T cell that may be present in the sample. The formation of an immunological complex if any, indicating the presence of the specific T cell type in the sample, is then detected and measured by suitable means.

Such methods include, but are not limited to, homogeneous and heterogeneous binding immunoassays, such as indirect immunofluorescence, radioimmunoassays (RIA), ELISA and Western blot analyses as discussed above. The antibodies may be labeled or unlabeled depending on the type of assay used. Labels which may be coupled to the antibodies are those known in the art and include but are not limited to enzymes, radionucleotides, fluorogenic and chromogenic substrates, cofactors, biotin/avidin, colloidal gold and magnetic particles. Modification of the antibodies allows for coupling by any known means to carrier proteins or peptides or to known supports, for example, polystyrene or polyvinyl microtiter plates, glass tubes or glass beads and chromatographic supports, such as paper, cellulose and cellulose derivatives, and silica.

Preferred assay techniques, especially for large-scale clinical screening of patient T cells include but are not limited to indirect immunofluorescence. For instance, the antibodies may be directly bonded to T cell specimens in solution or in situ in histological specimens and detected by fluorescence microscopy.

The antibodies are also suitable for use as therapeutic agents. For instance, the antibodies may be used unaltered or coupled to toxins including but not limited to ricin and diphtheria toxin and administered to a patient. Antibodies used alone are capable of fixing complement and initiating cytolysis of the target cell. Once the antibodies bind to the specific T cell, they cause the death or removal of the T cell and thus ameliorate the dysfunction caused by the T cells. The antibodies are generally administered with a pharmaceutically acceptable carrier or vehicle therefor. A pharmaceutically acceptable carrier is one that does not cause an adverse physical reaction upon administration and one in which the antibodies are sufficiently soluble and retain their activity to deliver a therapeutically effective amount of the compound. The therapeutically effective amount and method of administration of the antibodies may vary based on the individual patient, the indication being treated and other criteria evident to one of ordinary skill in the art. A therapeutically effective amount of the antibodies is one sufficient to induce death or removal of a sufficient number of the specific T cells to ameliorate the dysfunction without causing significant side effects such as non-specific T cell lysis or organ damage. The route(s) of administration useful in a particular application are apparent to one or ordinary skill in the art.

Routes of administration include, but are not limited to, parenteral, and direct injection into an affected site. Parenteral routes of administration include but are not limited to intravenous, intramuscular, intraperitoneal and subcutaneous. For most T cell dysfunctions, intravenous administration is preferred, but where the dysfunction is localized, such as in arthritis, direct injection to the affected site will result in increased effectiveness and decreased side effects such as non-specific organ damage.

The invention also encompasses antibodies made in response to the SA reactive T cells and which recognize TCR Vβ proteins. Such antibodies can be either polyclonal or monoclonal. Methods for making both types of antibodies are well known in the art. Methods of immunization and antibody production, purification and characterization are known in the art and need not be described in detail. The preferred antibodies are monoclonal (mAb) and are made by any method known in the art, for instance by the method described by Kohler and Milstein, "Continuous Cultures of Fused Cells Secreting Antibody of Predefined Specificity", Nature, 256:495–497 (1975) which is incorporated herein by reference.

The present invention includes compositions of the antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, subcutaneous or direct injection into a joint or other affected area.

Antibodies used in therapeutics suffer from several drawbacks such as a limited half-life and propensity to elicit an immune response. Several methods have been proposed to overcome these drawbacks. Antibodies made by these methods are encompassed by the present invention and are included herein. The use of the words herein "antibodies" and "mAb" include the specific embodiments discussed below. One such method is the "humanizing" of antibodies by cloning the gene segment encoding the antigen binding region of the antibody to the human gene segments encoding the remainder of the antibody. Only the binding region of the antibody is thus recognized as foreign and is much less likely to cause an immune response. An article describing such antibodies is Reichmann et al., "Reshaping Human Antibodies for Therapy", Nature 332:323–327 (1988), which is incorporated herein by reference. Another method to avoid the drawbacks found in antibody therapy can be found in the use of peptide analogues which mimic the antigen binding region of the antibody but are not themselves antibodies. An article describing such antibody mimetics is Saragovi et al., "Design and Synthesis of a Mimetic from an Antibody Complementarity-Determining Region", Science, 253:792–795 (1991), which is incorporated herein by reference.

The following Examples are meant to illustrate but not limit the present invention.

Example 1

Reagents Used in Succeeding Examples

Staphylococcal enterotoxins SEA, SEB, $SEC_1$, $SEC_2$, $SEC_3$ and SEE as well as toxic shock syndrome toxin, TSST-1, were obtained from Toxin Technology, Madison, WI and used according to the manufacturer's instructions. Partially purified MAM was isolated from *M. arthritidis* culture supernatants according to the method described by Atkin et al., (1986). All SA were used at a final concentration predetermined to be optimal for T cell proliferation, 1:4000 for MAM and 10–25 ng/ml for the Staphylococcal-derived SA.

Example 2

Isolation and Fractionation of Lymphocytes

Fresh peripheral blood or tonsil lymphocytes were isolated by Ficoll-Hypaque centrifugation according to the manufacturer's instructions. T cells were isolated from non-T cells by E-rosette formation with neuraminidase-treated sheep red blood cells according to the method described by Kaplan and Clark, "An Improved Rosetting Assay for Detection of Human T Lymphocytes", J. Immunol. Met., 5:131–135 (1974), and a second Ficoll-Hypaque centrifugation. Residual T cells were removed from the non-T cell fraction by treatment with anti-T3 antibodies obtained from hybridoma ATCC CRL 8001 (OKT3) obtained from ATCC, followed by the addition of magnetic beads coated with goat anti-mouse antibody and physical separation of the bead-bound T cells utilizing a magnet according to the manufacturer's instructions (Dynal, Inc., Great Neck, N.Y.).

Example 3

Generation of SA-reactive T helper (T) cell lines $CD4^+$ peripheral blood T cells were isolated from unselected T cell populations obtained as described in Example 2, by incubating the T cells with an excess of anti-CD8 mAb followed by washing and physical removal of T cells binding antibody to CD8 utilizing magnetic beads coated with goat anti-mouse antibody and a magnet according to the manufacturer's instructions (Dynal). The $CD4^+$-enriched populations were cocultured with X-irradiated autologous antigen presenting cells (APC) and either MAM or SEE. After 5 days, semi-purified human IL-2 (Electro-Nucleonics, Inc., Fairfield, N.J.) was added at a final concentration of 5%. Cultures were retriggered weekly with APC, and the relevant SA, and expanded in the presence of IL-2. Cell lines were maintained in culture media consisting of RPMI 1640 (Gibco Laboratories, Grand Island, N.Y.) containing 10% fetal bovine serum (fbs) (Whittaker, Mass. Bioproducts, Walkersville, Md.), penicillin and streptomycin (50 μg/ml, Gibco), and 2 mM glutamine (Gibco).

Example 4

CD23 Induction assay

The specific interaction of SA-reactive CD4+ human T cells and SA-bearing B cells results in the rapid expression of the CD23 activation antigen on a fraction of the resting B cell pool. Friedman et al., "A Potential Role for Microbial Superantigens in the Pathogenesis of Systemic Autoimmune Disease" Arthr & Rheum., 34:468 (1991).

The induction of B cell surface CD23 expression by $T_h$ cells has been detailed previously. Crow et al., (1986). Briefly, $5 \times 10^5$ purified tonsillar B cells were cultured in final medium with $1.5 \times 10^5$ X-irradiated CD4+ MAM- or SEE-reactive TCL cells. Cultures were supplemented with final medium alone or medium containing an optimal concentration of the various SA (MAM was used at a 1:4,000 dilution, whereas the other SA were used at 100 ng/ml). After 16 hours, B cells were assayed for CD23 expression by indirect immunofluorescence staining utilizing mAb $EBVCS_2$ (generously donated by Dr. Bill Sugden and Stan Metzenberg, Madison, Wis.) and counterstained with fluorescein-conjugated $F(ab')^2$ fragments of goat anti-mouse IgG according to the manufacturer's instructions (Tago, Inc., Burlingame, Calif.). The percentage of positively staining cells was determined by analysis on an Ortho IIs cytofluorograph (Ortho Diagnostic Systems, Inc., Westwood, Mass.).

The results obtained show that CD4+ SEE-reactive TCL cells induce optimal CD23 expression on B cells bearing TSST-1 or any of the SEs, but, as shown in Example 7, trigger little CD23 expression by MAM bearing B cells. This functional evidence of crossreactivity by SA-activated TCL cells is consistent with reports that activated human T cells are somewhat promiscuous in their proliferative responses to the staphylococcal-derived SA. Fleischer et al. (1991). Importantly, however, the patterns of CD23 expression observed suggest that MAM and SEE-specific human T cells show little cross-reactivity and may therefore utilize different TCR Vβ gene products. Thus, the SEE-reactive TCL provide an excellent comparison for screening MAM-specific TCR mAbs.

Example 5

Generation of Monoclonal Antibodies

In order to generate mAb to a clonal population of T cells, Balb/c mice were immunized on 4 occasions with $1 \times 10^7$ MAM-reactive TCL cells in 100 μl phosphate buffered saline (PBS, 10 mM $NAPO_4$, 150 mM NaCl, pH 7.2) which had been expanded in long-term culture (7 weeks) by weekly restimulation with autologous APC and MAM as described in Example 2. Essentially, the method described by Kohler and Milstein (1975) was used to produce the mAb. Briefly, three days after the final immunization, the mice were sacrificed and their splenocytes fused with the HGPRT deficient myeloma cell line SP2/0 or NS-1. Hybridomas which demonstrated reactivity with a small fraction of freshly isolated (resting) peripheral T cells were screened against the MAM-reactive TCL used for immunization and an SEE-reactive TCL-derived from the same donor. The presence of antibodies was detected by indirect immuofluorescence. Briefly, two color immunofluorescence was prepared by first incubating $5 \times 10^5$ cells with various mAb for 30 min. at room temperature. This was followed by 3 washes in PBS-BSA 1%, azide 0.2% and goat anti-mouse Ig-FITC (GAM-FITC) for 30 min. at room temperature. The cells were washed 3 times and incubated with a negative control IgG1 mAb for 30 min. at room temperature to quench free GAM-FITC binding sites. The cells were washed 3 times and incubated with phycoerythrin (PE) labeled anti-CD4 or anti-CD8 mAb (UBI/Olympus, Lake Success, NY) for 30 min. at room temperature. The cells were finally washed 3 times and analyzed on an ORTHO cytofluorograph. The results shown in Table I represent the ratio of double positive (FITC +PE) cells over total CD4 or CD8 positive cells expressed as a percentage. In this manner, a mAb termed Cl, was identified.

As shown in FIG. 3, Cl stains between 3–6% of peripheral T cells, >60% of the MAM-reactive TCL used as immunogen, and virtually no SEE-reactive TCL cells. Immunoprecipitation studies (FIG. 4) showed that mAb Cl recognizes a disulfide-linked heterodimer consistent with the α/β TCR. Finally, as with other TCR mAb specific for V gene products, Cl recognizes a small subset of peripheral T cells from all donors tested, including samples of cord blood T cells. While Cl+ cells are found among both CD4+ and CD8+ T cells, some donors show selective enrichment of Cl+ T cells in one or the other T cell subset (Table I).

mAb Cl was utilized to screen a number of SA-reactive TCL propagated in vitro. PBL were activated weekly with X-irradiated autologous APC and the indicated SA. The percentage of T cells staining with each of the anti-TCR mAbs was assessed each week 6 days after retriggering with X-irradiated APCs and SA.

Cord blood lymphocytes and PBL obtained from normal adult donors were analyzed by two-color immunofluorescence staining for distribution of Cl+ T cells in the CD4+ and CD8+ T cell subsets. Single color immunofluorescence was performed according to the method described by Crow et al. (1986).

TABLE I

Percentage of Cl+ T cells in CD4+ and CD8+ subpopulations

|  |  | Cl+ CD4+ | Cl+ CD8+ |
|---|---|---|---|
| Adult blood | 1 | 14.00 | 3.77 |
|  | 2 | 6.40 | 2.30 |
|  | 3 | 7.98 | 5.56 |
|  | 4 | 5.65 | 7.87 |
|  | 5 | 6.63 | 11.32 |
| Cord bloods | 1 | 7.69 | 3.76 |
|  | 2 | 4.75 | 3.98 |
|  | 3 | 3.99 | 3.20 |
|  | 4 | 3.45 | 4.48 |
|  | 5 | 5.65 | 7.87 |
| Mean ± SD |  | 6.62 ± 2.83 | 5.41 ± 2.64 |

TABLE II

Peripheral Blood T-cells Triggered With MAM are Highly Enriched in Cl

|  | Superantigen Stimulus | Percentage of T-cells Staining Positively With Anti-TCR mAbs | | | | |
|---|---|---|---|---|---|---|
|  |  | Cl | C37 | OT145 | S511 | Ti3a |
| Primary culture | MAM | 55.6 | 0.0 | 2.5 | 2.5 | 5.6 |
|  | TSST | 0.6 | 1.3 | 2.8 | 0.8 | 1.9 |
|  | SEA | 5.1 | 0.6 | 2.9 | 2.9 | 5.9 |
|  | SEB | 26.5 | 0.4 | 2.7 | 9.0 | 1.5 |
|  | SEE | 3.0 | 3.4 | 1.2 | 0.2 | 12.5 |
|  | SEC1 | 17.8 | 4.8 | 3.0 | 7.3 | 5.2 |
|  | SEC2 | 15.1 | 1.8 | 0.0 | 7.1 | 1.7 |

TABLE II-continued

Peripheral Blood T-cells Triggered
With MAM are Highly Enriched in C1

| | Superantigen Stimulus | Percentage of T-cells Staining Positively With Anti-TCR mAbs | | | | |
|---|---|---|---|---|---|---|
| | | C1 | C37 | OT145 | S511 | Ti3a |
| | SEC3 | 9.2 | 4.1 | 1.9 | 4.5 | 6.2 |
| Secondary | MAM | 39.4 | 1.2 | 0.2 | 2.8 | 2.7 |
| culture | TSST | 0.2 | 0.0 | 1.1 | 0.0 | 0.0 |
| | SEA | 1.2 | 0.0 | 0.0 | 0.0 | 0.0 |
| | SEB | 10.1 | 0.6 | 2.2 | 6.4 | 0.7 |
| | SEE | 0.6 | 1.2 | 0.5 | 0.1 | 15.3 |
| | SEC1 | 9.4 | 1.0 | 1.4 | 2.0 | 3.1 |
| | SEC2 | 15.5 | 1.6 | 0.0 | 5.0 | 0.4 |
| | SEC3 | 6.9 | 0.0 | 0.0 | 0.8 | 0.0 |
| Tertiary | MAM | 32.4 | 0.2 | 0.0 | 1.5 | 2.7 |
| culture | TSST | 0.0 | 0.1 | 0.3 | 2.6 | 1.6 |
| | SEA | 0.7 | 0.3 | 0.4 | 0.7 | 0.9 |
| | SEB | 7.3 | 0.5 | 0.0 | 3.3 | 3.3 |
| | SEE | 0.1 | 0.3 | 2.1 | 1.3 | 11.9 |
| | SEC1 | 8.7 | 0.6 | 0.7 | 2.5 | 0.9 |
| | SEC2 | 17.0 | 0.0 | 0.0 | 7.4 | 0.0 |
| | SEC3 | 6.2 | 0.0 | 0.1 | 1.8 | 0.2 |

As shown (Table II) short term activation of peripheral T cells with a panel of SA demonstrates a clear enrichment of C1$^+$ cells among the T cells activated by MAM and several of the SE with which MAM-specific TCL cells crossreact in the CD23 induction assay, in particular, SEB, SEC1, SEC2, SEC3. In contrast, C1$^+$ T cells are not well represented among non-crossreactive TSST-1 or SEE-activated T cells. T cells expanded by weekly retriggering with SEB or SEC 1 and autologous APC show a marked fall off in the percentage of C1$^+$ T cells (Table II).

These results indicate that SA such as SEB are recognized by T cells expressing several TCR Vβ gene family products among which C1$^+$ T cells are a minor component with a relatively low binding affinity for SEB. In contrast, C1$^+$ T cells are greatly expanded in short-term cultures of MAM-activated T cells and remain well represented. In the experiment presented in Table 3, (described in Example 8) the percentage of C1$^+$ T cells decreases somewhat over time in the culture stimulated weekly by MAM. However, in most experiments, C1$^+$ T cells represent between 50 and 60% of TCL repetitively triggered with MAM (FIG. 3). In FIG. 3, PBL shown in the upper right; the CD4$^+$ MAM-reactive T cell line used for immunization shown in the lower right; or a CD4$^+$ SEE-reactive T cell derived from the same donor shown in the lower left were analyzed by indirect immunofluorescence staining for reactivity with C1. Background staining of PBL with PBS and fluoresceinated anti-mouse Ig is shown in the upper left.

The results obtained indicate that C1$^+$ T cells comprise a stable population of 15–20% of SEC$_2$ reactive TCL cells. These results suggest that C1$^+$ T cells represent the major population of human T cells reactive with MAM, and a significant fraction of the SEC$_2$-responsive T cell pool.

Example 6

Generation of TCL enriched for TCR V gene usage

Tonsil T cell aliquots were incubated at room temperature with saturating concentrations of non-cross-reactive TCR V gene specific mAb: C37 (Vβ 5.2/5.3) Wang et al., "A Monoclonal Antibody Detecting a Shared Determinant on the Human T Cell Antigen Receptor Molecule", Hybridoma, 5:179 (1986), OT145 (Vβ 6.7a) Posnett et al., "Inherited Polymorphism of the Human T Cell Antigen Receptor Detected by a Monoclonal Antibody" Proc Natl Acad Sci USA, 83:7888 (1986); and Li et al., "Allelic Variations in the Human T Cell Receptor Vβ 6.7 Gene Products", J. Exp. Med., 171:221 (1990) and C1. After 30 minutes, cells were washed 3 times, resuspended in final medium and cultured at a final concentration of 0.5×10$^6$/ml in the presence of goat anti-mouse antibody-coated magnetic beads according to the manufacturer's instructions (Dynal). Beads were added at a ratio of 20 beads to 1 target T cell. After 5 days, magnetic beads were removed, the T cells washed and recultured with IL-2 alone for 48 hours. Cultures were maintained with IL-2 and weekly feeding with periodate-treated allogeneic non-T feeder cells.

These cultures become highly enriched in T cells expressing the relevant Vβ gene, depending on the initial mAb used for stimulation. Usually, this occurs over a 6-day period. Occasionally, a second cycle of stimulation was required to achieve greater than 95% specific Vβ expression. At the time these TCL were utilized as effectors in the cytolytic assay or for RNA isolation as described in Example 10, each was virtually 100% for T cells expressing the appropriate TCR Vβ gene products.

Example 7

Assay of SA-dependent Cytolysis

Figure 4A:
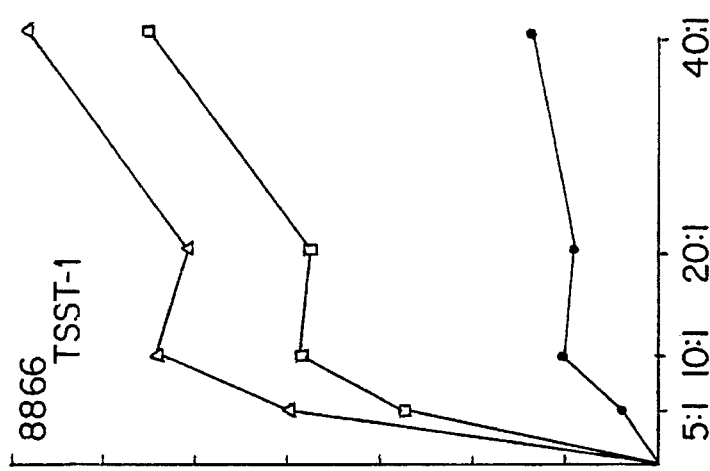
FIG. 4A is a line graph depicting $^{51}$Cr release by control 8866 B cells lysed by activated T cells.
Figure 4B:
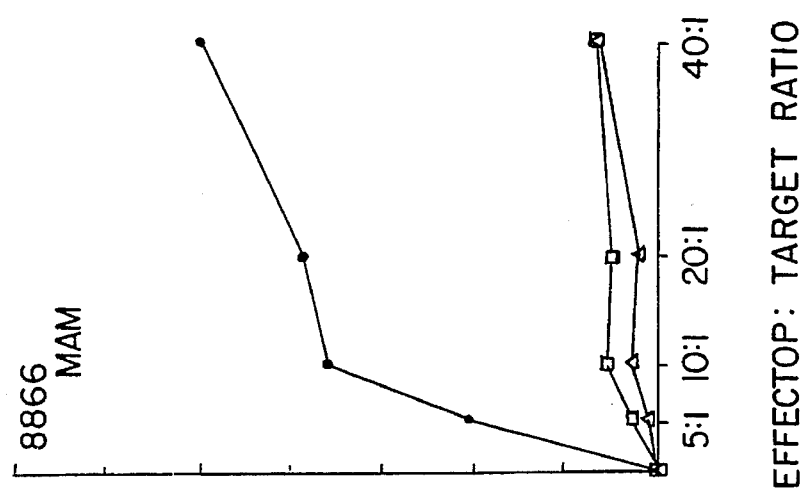
FIG. 4B is a line graph depicting $^{51}$Cr release by MAM-treated 8866 B cells lysed by activated T cells.
Figure 4C:
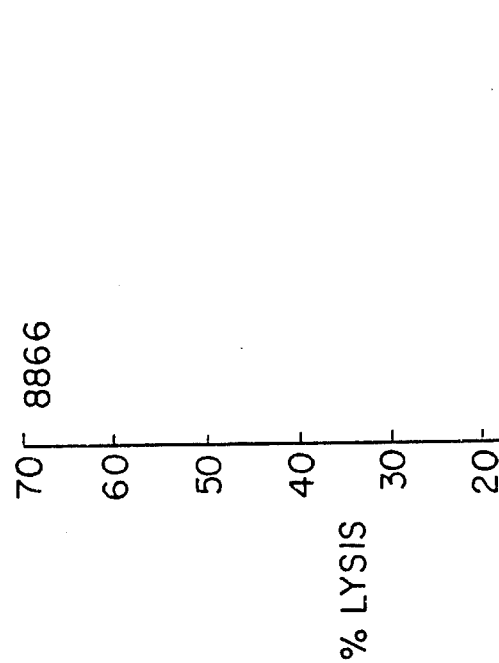
FIG. 4C is a line graph depicting $^{51}$Cr release by TSST-treated 8866 B cells lysed by activated T cells.

In order to show that the MAM-reactive T cell population contains both a C1$^+$ and a C1– population of T cells, a functional assay was performed. Anti-TCR mAbs are mitogenic; this characteristic was used to formally prove that C1$^+$ T cells are MAM-reactive by allowing the selective activation and expansion of T cells expressing the relevant TCR epitope. Aliquots of tonsillar T cells were treated with saturating concentrations of C1 or either of two non-cross-reactive TCR Vβ gene product specific mAb: C37 (Vβ 5.2/5.3, and OT145 (Vβ6.7a). TCL were generated as described in Example 2. These lines are virtually pure with respect to reactivity with the relevant anti-TCR mAb (FIG. 4).

TCL cells were assayed for cytolytic activity in a 4-hour [$^{51}$Cr] release assay according to the method described by Friedman et al., "Amplification of Altered Self-Reactive Cytolytic T Lymphocyte Responses by Cloned Allospecific Human T Helper Cells", J. Clin. Invest., 82:1722 (1988) which is incorporated herein by reference, utilizing an MHC class II antigen-bearing target cell line, B cell lymphoblastoid cell line 8866. Briefly, 8866 cells were incubated for 2 hours at 37° C. with 0.1 mCi [$^{51}$Cr] in the presence of final medium alone, or the indicated SA.

Peripheral blood T cells were expanded in culture by weekly activation with mAb C1, goat anti-mouse Ig-coated magnetic beads, and IL-2 in order to generate a C1$^+$ TCL. In addition, an aliquot of the peripheral T cell population was depleted of C1$^+$ cells utilizing the magnetic beads, and activated with MAM, autologous X-irradiated APC's, and IL-2. This MAM-reactive C1$^-$ TCL was retreated weekly to insure complete depletion of residual C1$^+$ T cells. At the time these TCL cells were used as effectors in the cytolytic assay (after 4 weeks of culture), less than 0.5% of the TCLs stained with C1. Both the MAM-reactive C$^-$ TCL and the C1$^+$ TCL were utilized as effector cells in a cytolytic assay against [$^{51}$Cr]-labeled 8866 target cells, either untreated or "pulsed" with SA as described above. Both TCL efficiently and specifically lyse MAM bearing target cells, suggesting a MAM reactive C1$^-$ T cell population.

Figure 5A:
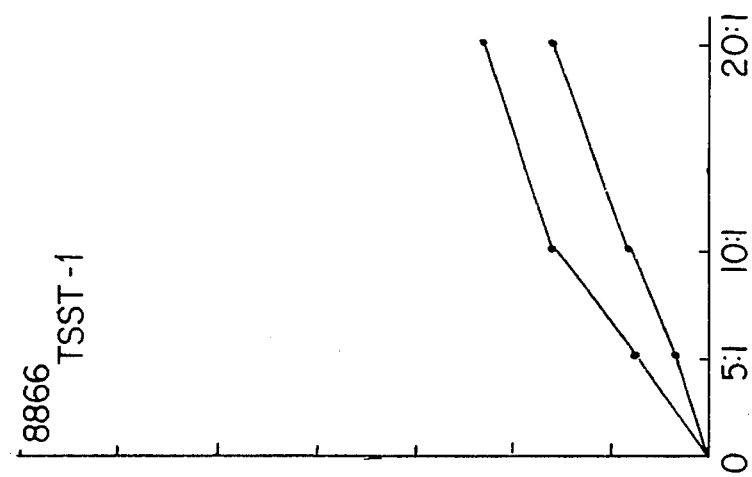
FIG. 5A is a line graph depicting $_5$Cr release by control 8866 B cells lysed by activated Cl+ T cells.
Figure 5B:
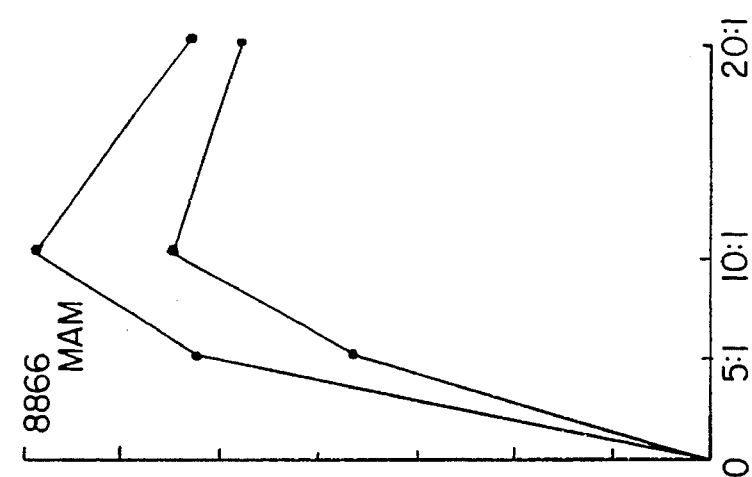
FIG. 5B is a line graph depicting $^{51}$Cr release by MAM-treated 8866 B cells lysed by activated Cl+ T cells.
Figure 5C:
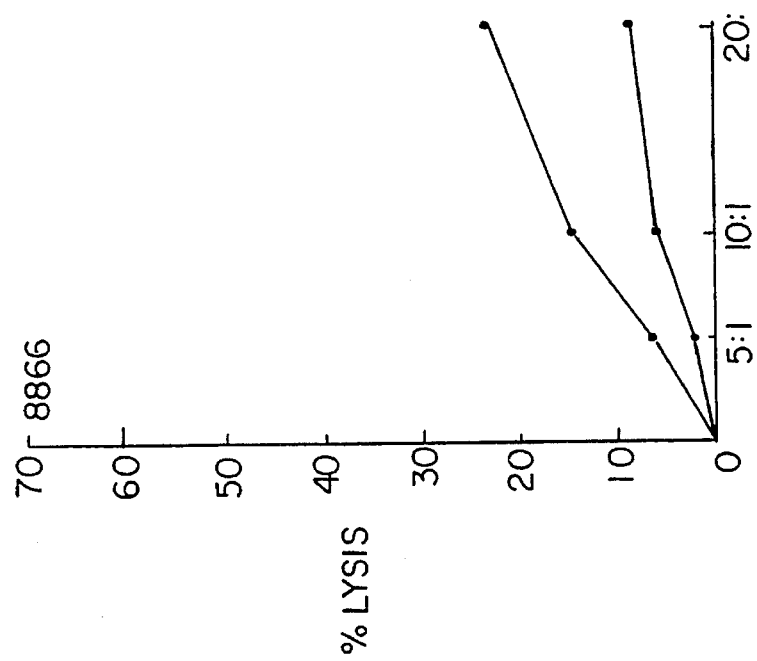
FIG. 5C is a line graph depicting 51Cr release by TSST-treated 8866 B cells lysed by activated CL+ T cells.

As shown in FIG. 5, both the MAM-reactive TCL and the C1$^+$ TCL specifically and efficiently lyse the MAM bearing 8866 target cells. Data are presented as mean percent lysis of target cells at each effector to target cell ratio. These data confirm that C1$^+$ T cells are MAM reactive. Taken together, these findings support the existence of a MAM-reactive human T cell population distinct from that which expresses the C1 epitope.

FIG. 4 shows the results obtained when tonsillar T cells, expanded in culture by weekly activation with an anti-TCR mAb, goat anti-Ig-coated magnetic beads, and IL-2, in triplicate at the effector to target ratios indicated in FIG. 4 for cytotoxic activity against [$^{51}$Cr] release assay. Target cells consisted of a lymphoblastoid B cell line 8866 either untreated (8866) or "pulsed" for one hour at 37° C. with MAM (8866$_{MAM}$) or TSST-1 (8866$_{TSST-1}$). Briefly, purified tonsillar B cells were cultured with medium alone or the indicated SA at 100 ng/ml, except MAM, which was used at 1/4000 dilution. CD4$^+$ MAM-reactive TCL cells or CD4$^+$ SEE-reactive TCL cells were added, cultures incubated for 16 hours, then analyzed for CD23 expression by indirect immunofluorescence staining. Depicted are the cytotoxic activities of C37 activated T cells; mAb 0T145 activated T cells; and C1 activated T cells. The phenotype of these three cell lines at the time of assay are as follows:

C37 activated=99% C37$^+$, 22% CD4$^+$, 77% CD8$^+$

OT145 activated=100% OT145$^+$; 16% CD4$^+$; 85% CD8$^+$;

C1 activated=99% C1$^+$43% CD4$^+$61% CD8$^+$

While each line contained a CD4$^+$ T cell fraction, CD8$^+$ T cells predominated, comprising 60–80% of the TCL population. A CD8$^+$ T cell-dependent function was therefore assessed, by determining if these TCL cells could lyse MHC class II positive target cells in a SA dependent manner. In the experiment depicted in FIG. 4, no significant lysis of untreated 8866 target cells by any of the TCL is observed. However, the C1$^+$ TCL selectively lyse MAM-bearing 8866 cells, while both the OT145$^+$ and C37$^+$ TCL cells effectively lyse TSST-1 bearing, but not MAM-bearing, targets. It should be noted that the proliferative response of human T cells to TSST-1 is reportedly dominated by the Vβ 2$^+$ fraction. Choi et al., "Selective Expansion of T Cells Expressing Vβ 2 in Toxic Shock Syndrome", J. Exp. Med., 172:981 (1990). The lysis of TSST-1 bearing targets by Vββ6.7a$^+$ and Vβ5.2/5.3$^+$ TCL cells therefore represents another example of the cross-reactivity of activated T cell responses to *S. aureus*-derived SA. Fleischer et al., "An Evolutionarily Conserved Mechanism of T Cell Activation by Microbial Toxins: Evidence for Different Affinities of T Cell Receptor Toxin Interaction" J. Immunol, 146:11 (1991)

The experiment depicted in FIG. 4 has been performed on three separate occasions utilizing C1$^+$ TCL independently derived from different donors. In all studies, the results are similar to those shown in FIG. 5. Thus, C1$^+$ T cells, activated and expanded with C1, demonstrate functional specificity for MAM.

Example 8

Immunoprecipitation of TCR Utilizing C1

A MAM-reactive TCL with 60% C1$^+$ T cells was radio-iodinated with lactoperoxidase and peroxide, using 25×10$^6$ cells and 2.5 mCi [$^{125}$I]. Cell lysis and immunoprecipitations with SPA-Sepharose and monoclonal antibodies were performed as previously described by Posnett et al., "A Novel Method for Producing Antipeptide Antibodies. Production of Site-Specific Antibodies to the T Cell Antigen Receptor β Chain", J. Biol. Chem., 263:1719 (1988).

Figure 2A:
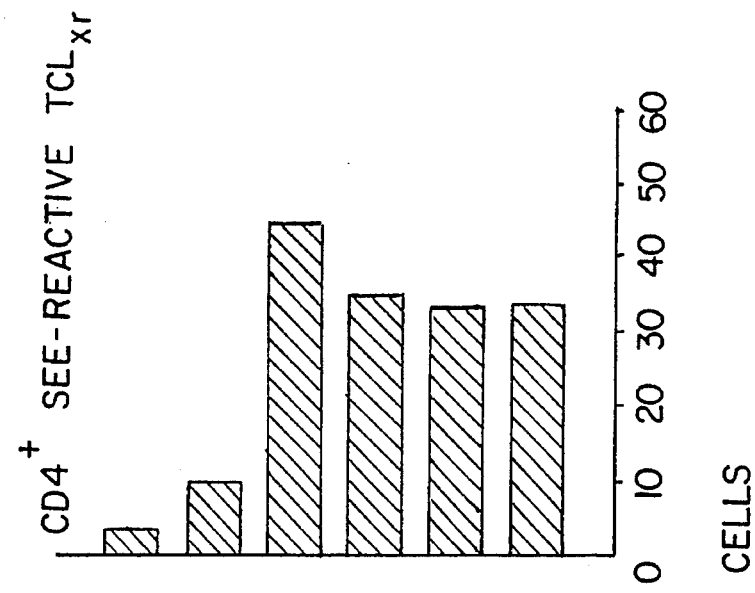
FIG. 2A is a bar graph depicting B cell CD23 expression in response to T cells exposed to the superantigen MAM.
Figure 2B:
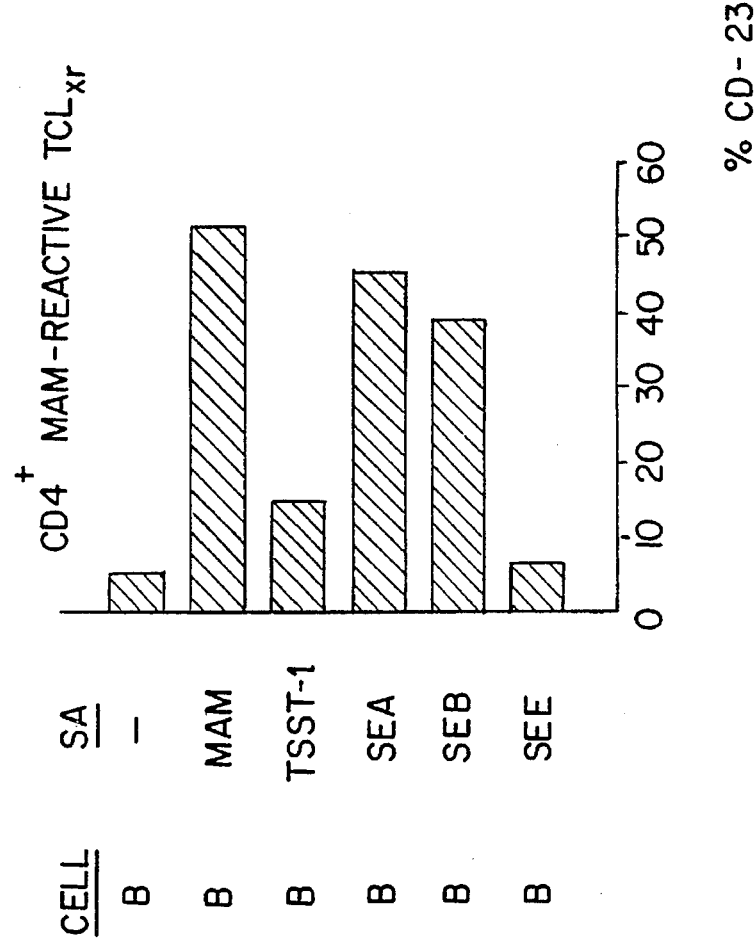
FIG. 2B is a bar graph depicting B cell CD23 expression in response to T cells exposed to the superantigen SEE.
Figure 3A:
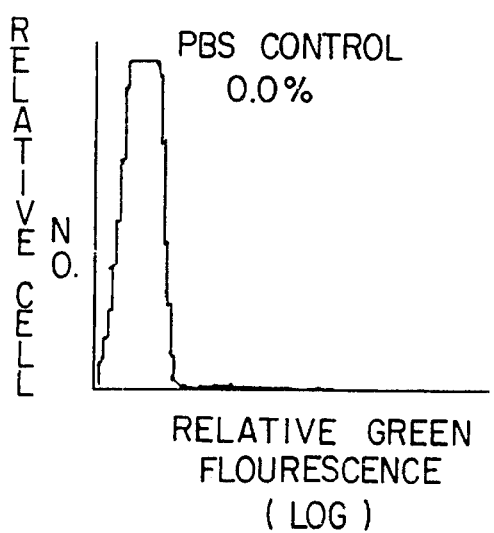
FIG. 3A is a line graph depicting control immunofluorescence of peripheral blood lymphocytes after incubation with PBS and fluoresceinated goat antimouse antibody.
Figure 3B:
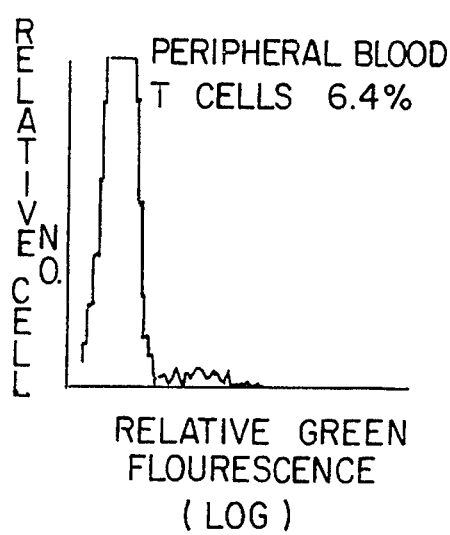
FIG. 3B is a line graph depicting immunofluorescence of peripheral blood lymphocytes after staining with monoclonal antibody CI followed by fluoresceinated goat anti-mouse antibody.
Figure 3C:
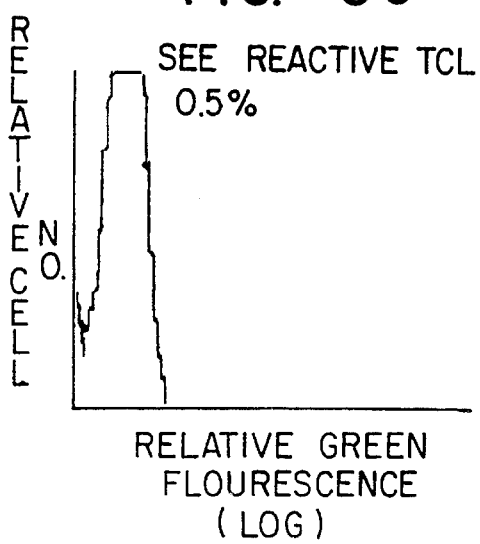
FIG. 3C is a line graph depicting immunofluorescence of SEE-reactive T cells after staining with monoclonal antibody Cl followed by fluoresceinated goat anti-mouse antibody.
Figure 3D:
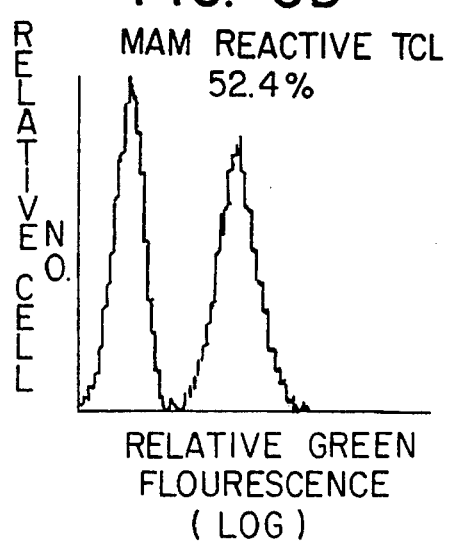
FIG. 3D is a line graph depicting immunofluorescence of MAM-reactive T cells after staining with monoclonal antibody Cl followed by fluoresceinated goat anti-mouse antibody.

The expansion of C1$^+$ cells in short-term cultures of SE-activated T cells (Table II) indicates that C1$^+$ T cells can account for the pattern of SA responsiveness associated with MAM-reactive TCL (FIG. 2). However, these data do not rule out the existence of C1$^-$ MAM-reactive T cells. Indeed, the observation that repetitive triggering of MAM-reactive T cells with MAM results in a TCL that is maximally 50–60% C1$^+$ provides indirect evidence that a C1$^-$ MAM-reactive T cell population exists. To address this point, aliquots of fresh peripheral T cells were depleted of C1$^+$, C37$^+$ or OT145$^+$ T cells by treatment with the relevant mAb followed by physical removal of the reactive T cells utilizing magnetic beads bearing goat anti-mouse IgG. Peripheral blood T lymphocytes were depleted of T cells reacting with anti-TCRmAbs C1 or C37 utilizing magnetic beads coated with anti-mouse IgG. Untreated or mAb-depleted T cells were assayed, in triplicate, for proliferative responses against medium alone, autologous APC, or the indicated SA in the presence of autologous APC. The percentage of C1$^+$ T cells present in each responder T cell population was detected by immunofluorescence staining. In Table III experiments 1 and 2 describe the results of separate studies involving two different normal donors.

TABLE III

C1 Depleted T-cells Proliferate in Response to MAM

| | Description of responder population | Media | [$^3$H]-Tdr incorporation (cpm) induced by: | | | |
|---|---|---|---|---|---|---|
| | | | APC$_{xr}$ % C1$^+$ | MAM APC$_{xr}$ | SEE APC$_{xr}$ | TSST-1 APC$_{xr}$ |
| Exp. 1 | E$^+$ | 3.5 | 85 | 6,681 | 37,978 | 39,313 | 69,033 |
| | E$^+$ C1 | 0.3 | 53 | 1,159 | 24,226 | 25,667 | 55,629 |
| | E$^+$ C37 | 2.8 | 2,969 | 1,837 | 25,509 | 23,847 | 59,855 |
| Exp. 2 | E$^+$ | 4.6 | 82 | 1,170 | 26,748 | 122,655 | 54,603 |
| | E$^+$ C1 | 0.9 | 267 | 1,348 | 27,721 | 99,509 | 46,956 |
| | E$^+$ C37 | 4.1 | 239 | 1,184 | 29,513 | 77,742 | 58,827 |

AS shown in Table III, while this procedure efficiently reduces or eliminates the C1$^+$ T cell pool, as detected by immunofluorescence staining, the proliferative response to MAM was not affected. It should be pointed out that T cell populations depleted of C1$^+$ cells maintain strong proliferative responses over a wide range of MAM concentrations (6 log dilutions). In additional studies, the cytolytic activity of a C1⁺ TCL and a MAM-reactive TCL depleted of C1⁺ cells, both derived from the same donor were compared.

Example 9

Analysis of TCR Vβ Gene by Polymerase Chain Reaction (PCR)

Three T cell lines were prepared by stimulating normal peripheral blood T cells with either OT145 (Vβ6.7), C37 (Vβ5.2/5.3) or C1 mAb as described in Example 8. Total cellular RNA was isolated from each cell line by the acid guanidinium thiocyanate-phenol-chloroform method. Chomczynski and Sacchi, "Single-step Method of RNA Isolation by Guanidinium Thiocyanate-Phenol-Chloroform Extraction", Anal. Biochem., 165:156 (1987).

cDNA was synthesized with reverse transcriptase, using an anti-sense Cβ primer the sequence of which is described below, according to the method described by Li et al., (1990).

The PCR was performed with a panel of Vβ specific sense primers, in parallel reactions where each Vβ primer was matched with the Cβ anti-sense primer situated 55 bp from the 5' end of the C region. Two paired Cβ primers were used as a positive control. Each cDNA preparation was tested for the optimal dilution. PCR conditions included primers at 0.5 µ, Replinase (Dupont) 2 U, buffer containing 3.0 mM $MgCl_2$ (20 buffer, Dupont), [$^{32}$P]-dCTP 20 µCi, cold dNTPs at 0.2 mM each in a final volume of 20 µl. Amplification was done for 1 min. at 94° C., 1 min at 51° C. and 1 min at 72° C. for 25 cycles.

PCR products were analyzed using polyacrylamide gel electrophoresis on a 5% polyacrylamide gel. The gel was dried and exposed to film.

| | | | | |
|---|---|---|---|---|
| Cβ | (anti-sense) | 5' | CTTCTGATGGCTCAAACAC | 3' (SEQ ID NO: 1) |
| Cα 5' | (sense) | 5' | GAACCCTGACCCTGCCGT | 3' (SEQ ID NO: 2) |
| Cα 3' | (anti-sense) | 5' | TCATAAATTCGGGTAGGATC | 3' (SEQ ID NO: 3) |
| Vβ 2 | (sense) | 5' | GTTTCTCATCAACCATGCAA | 3' (SEQ ID NO: 4) |
| Vβ 6 | (sense) | 5' | TCAGGTGTGATCCAATTTC | 3' (SEQ ID NO: 5) |
| Vβ 5.3/5.2 | (sense) | 5' | GTCAGGGGCCCCAGTTTAT | 3' (SEQ ID NO: 6) |
| Vβ 17 | (sense) | 5' | ACAGCGTCTCTCGGGAGA | 3' (SEQ ID NO: 7) |

Specific PCR amplification of Vβ17 gene products from a C1⁺ TCL was performed. The PCR amplified cDNA from three cell lines (OT145⁺, C37⁺, C1⁺) were obtained with Cα primer (positive control), Cβ-Vβ2 primers (negative control), Cβ-Vβ5.2/5.3 primers, Cβ-Vβ6 primers or Cβ-Vβ17 primers. specific bands are indicated with arrows. In each case, the bands migrated as expected based on the estimated size of the amplified segment.

TCL were prepared with three mAb: OT145 (Vβ6.7α), C37 (Vβ5.2/5.3), and C1, as described above. Each of these polyclonal T cell lines contained >98% cells positive with the relevant mAb. RNA was isolated and cDNA synthesized with reverse transcriptase. Aliquots of cDNA were PCR amplified with different primer combinations. The results obtained showed that each cell line expressed a specific Vβ. As expected, the OT145⁺ cells expressed Vβ6, and the C37⁺ cells expressed Vβ5.2/5.3. The C1⁺ cells expressed Vβ17. None of these TCL expressed Vβ2 and all of them expressed Cα. In other experiments the C1⁺ cell line was analyzed with primers specific for Vβ1-Vβ20. No primer combinations other than Vβ17-Cβ amplified a β-chain product. Thus, Vβ17 appears to represent the sole Vβ gene product recognized by C1. Vβ17 is thought to represent a Vβ family with a single gene copy based on counting bands on Southern blots. Robinson, "The Human T Cell Receptor β Chain Gene Complex Contains at Least 57 Variable Gene Segments: Identification of Six Vβ Genes in Four New Gene Families", J. Immunol., 146:4392 (1991); Concannon et al., "Diversity and Structure of Human T Cell Receptor β Chain Variable Region Genes", Proc. Natl. Acad. Sci. USA, 83:6598 (1986); and Kimura et al, "Sequences and Repertoire of the Human T Cell Receptor α and β Chain Variable Region Genes in Thymocytes", Eur. J. Immunol., 17:375 (1987).

We claim:

1. A method of obtaining polyclonal anti-T cell antibodies specific to a subset of T cells having common TCR Vβ gene usage comprising the steps of:
    (a) incubating T cells with an effective amount of a superantigen under conditions and for a time sufficient to allow division and growth of T cells reactive to the superantigen;
    (b) injecting the incubated T cells from step (a) into a mammal; and
    (c) removing blood from the mammal and isolating from said blood serum containing the antibodies from the mammal.

2. The method according to claim 1 wherein the superantigen is derived from a source selected from the group consisting of bacteria and retroviruses.

3. The method according to claim 2 wherein the bacterially derived superantigens are selected from the group consisting of staphylococci, mycoplasma and streptococci.

4. The method according to claim 3 wherein the superantigen is the *Mycoplasma arthritidis*-derived superantigen MAM.

5. A method of obtaining anti-T cell monoclonal antibodies specific to a subset of T cells having common TCR Vβ gene usage comprising the steps of:

(a) incubating T cells with an effective amount of a superantigen under conditions and for a time sufficient to allow division and growth of T cells reactive to the superantigen;

(b) injecting the incubated T cells from step (a) into a mouse;

(c) fusing splenocytes from the mouse with a plasmacytoma cell line to produce a multiplicity of hybridomas; and (d) selecting a hybridoma secreting the anti-T cell antibody from among those produced in step (c).

6. The method according to claim 5 wherein the superantigen is derived from a source selected from the group consisting of bacteria and retroviruses.

7. The method according to claim 6 wherein the bacterially derived superantigens are selected from the group consisting of staphylococci, mycoplasma and streptococci.

8. The method according to claim 7 wherein the superantigen is the *Mycoplasma arthritidis*-derived superantigen MAM.

9. A method for obtaining unique polyclonal anti-T cell antibodies specific to a subset of T cells having common TCR Vβ gene usage, comprising the steps of:

contacting T cells with pre-existing polyclonal antibodies specific to a first subset of T cells having common TCR Vβ gene usage;

incubating the cells and antibodies for a time and under conditions sufficient to allow immune complexes to form between the antibodies and the cells;

removing the immune complexes to obtain a T cell sample enriched for T cells not recognized by the antibodies;

incubating the T cell sample with an effective amount of a superantigen under conditions and for a time sufficient to allow division and growth of T cells;

injecting the resulting T cells into a mammal; and removing blood from the mammal and isolating from said blood serum containing anti-T cell antibodies specific to a second subset of T cells having common TCR Vβ gene usage.

10. The method according to claim 9 further comprising repeating the steps of claim 9, wherein the pre-existing antibodies comprise polyclonal anti-T cell Vβ antibodies produced by the method of claim 9, so as to develop a panel of polyclonal anti-T cell antibodies wherein each of said antibodies recognizes a separate Vβ gene product.

11. A method for obtaining unique monoclonal anti-T cell antibodies specific to a subset of T cells having common TCR Vβ gene usage, comprising the steps of:

contacting T cells with pre-existing polyclonal antibodies specific to a first subset of T cells having common TCR Vβ gene usage;

incubating the cells and antibodies for a time and under conditions sufficient to allow immune complexes to form between the antibodies and the cells;

removing the immune complexes to obtain a T cell sample enriched for T cells not recognized by the antibodies;

incubating the T cell sample with an effective amount of a superantigen under conditions and for a time sufficient to allow division an d growth of T cells;

injecting the resulting T cells into a mouse;

fusing splenocytes from the mouse with a plasmacytoma cell line to produce a multiplicity of hybridomas; and selecting a hybridoma secreting anti-T cell antibodies specific to a second subset of T cells having common TCR Vβ gene usage from among those produced in the previous step.

12. The method according to claim 11 further comprising repeating the steps of claim 11, wherein the pre-existing antibodies comprise polyclonal anti-T cell Vβ antibodies produced by the methods of claims 9 or 10, so as to develop a panel of monoclonal anti-T cell antibodies wherein each of said antibodies recognizes a separate Vβ gene product.

13. A method for obtaining unique monoclonal anti-T cell antibodies specific to a subset of T cells having common TCR Vβ gene usage, comprising the steps of:

contacting T cells with pre-existing monoclonal antibodies specific to a first subset of T cells having common TCR Vβ gene usage;

incubating the cells and antibodies for a time and under conditions sufficient to allow immune complexes to form between the antibodies and the cells;

removing the immune complexes to obtain a T cell sample enriched for T cells not recognized by the antibodies;

incubating the T cell sample with an effective amount of a superantigen under conditions and for a time sufficient to allow division and growth of T cells;

injecting the resulting T cells into a mouse;

fusing splenocytes from the mouse with a plasmacytoma cell line to produce a multiplicity of hybridomas; and selecting a hybridoma secreting anti-T cell antibodies specific to a second subset of T cells having common TCR Vβ gene usage from among those produced in the previous step.

14. The method according to claim 13 further comprising repeating the steps of claim 13, wherein the pre-existing antibodies comprise monoclonal anti-T cell Vβ antibodies produced by the method of claim 13, so as to develop a panel of anti-T cell antibodies wherein each of said antibodies recognizes a separate Vβ gene product.

* * * * *